(12) United States Patent
King, III

(10) Patent No.: US 11,083,233 B2
(45) Date of Patent: Aug. 10, 2021

(54) THERAPEUTIC GLOVE FOR SUPPORT AND EXERCISE OF FINGERS AND WRIST

(71) Applicant: Felix King, III, Oxon Hill, MD (US)

(72) Inventor: Felix King, III, Oxon Hill, MD (US)

(73) Assignee: Felix King, III, Oxon Hill, MD (US)

( * ) Notice: Subject to any disclaimer, the term of this patent is extended or adjusted under 35 U.S.C. 154(b) by 10 days.

(21) Appl. No.: 16/167,341

(22) Filed: Oct. 22, 2018

(65) Prior Publication Data

US 2019/0216145 A1 Jul. 18, 2019

Related U.S. Application Data

(60) Provisional application No. 62/707,066, filed on Oct. 20, 2017.

(51) Int. Cl.
| | |
|---|---|
| *A41D 19/00* | (2006.01) |
| *A63B 21/00* | (2006.01) |
| *A63B 23/16* | (2006.01) |
| *A63B 21/055* | (2006.01) |
| *A61N 1/00* | (2006.01) |
| *A61N 1/04* | (2006.01) |
| *A61N 1/36* | (2006.01) |
| *A61H 7/00* | (2006.01) |
| *A63B 71/14* | (2006.01) |

(52) U.S. Cl.
CPC ......... *A41D 19/0024* (2013.01); *A61H 7/001* (2013.01); *A61N 1/00* (2013.01); *A61N 1/0484* (2013.01); *A61N 1/36014* (2013.01); *A63B 21/00065* (2013.01); *A63B 21/0552* (2013.01); *A63B 21/4019* (2015.10); *A63B 21/4025* (2015.10); *A63B 23/16* (2013.01); *A61H 2201/10* (2013.01); *A61H 2201/1253* (2013.01); *A61H 2201/165* (2013.01); *A61H 2201/1635* (2013.01); *A61H 2205/065* (2013.01); *A63B 71/141* (2013.01); *A63B 2209/10* (2013.01); *A63B 2213/004* (2013.01)

(58) Field of Classification Search
CPC ............ A63B 21/4019; A63B 21/0552; A63B 21/0057; A63B 21/00065; A63B 21/16; A63B 21/4025; A63B 71/141; A63B 2209/10; A61H 2205/065; A61N 1/0285; A61N 1/0288; A61N 1/36014; A61N 1/0484; A61N 1/00; A61N 7/001; A61N 2201/10; A61N 2201/165; A61N 2201/1253; A61N 2201/1635; A61N 2213/004
USPC ................................. 601/40; 482/44, 47, 48
See application file for complete search history.

(56) References Cited

U.S. PATENT DOCUMENTS

| | | |
|---|---|---|
| 19,814 A | 3/1858 | Monestier |
| 248,980 A | 11/1881 | Atkins |
| 623,592 A | 4/1899 | Bonney |
| 2,736,034 A | 2/1956 | Fredenhagen et al. |

(Continued)

*Primary Examiner* — Jocelyn Bravo
(74) *Attorney, Agent, or Firm* — Staas & Halsey LLP

(57) ABSTRACT

A wearer is able to exercise the posterior (flex) muscles of the hand. Elastic bands attached to the glove cause the fingers to contract toward the palm and provide resistance when the fingers are straightened. The elastic bands are secured by bandlettes attached to the fingers and thumb of the glove. Palmlettes are attached at the base of the palm to keep the bands clear of the palm while wearing, so that ordinary tasks can be performed while wearing the glove.

4 Claims, 6 Drawing Sheets

(56) References Cited

U.S. PATENT DOCUMENTS

| | | | |
|---|---|---|---|
| 3,347,547 A * | 10/1967 | Hynes | A63B 23/16 482/47 |
| 3,497,218 A * | 2/1970 | Johnston | A63B 69/0002 473/458 |
| 3,612,521 A | 10/1971 | Wendeborn | |
| 3,880,426 A * | 4/1975 | Morse | A63D 5/00 473/61 |
| 4,368,883 A * | 1/1983 | Tiktin | A63B 21/065 2/162 |
| 4,815,729 A | 3/1989 | Stefanski | |
| 4,875,469 A | 10/1989 | Brook et al. | |
| 5,062,625 A | 11/1991 | Vonk | |
| 5,447,490 A * | 9/1995 | Fula | A63B 21/0004 482/124 |
| 5,514,052 A | 5/1996 | Charles et al. | |
| 5,527,244 A | 6/1996 | Waller et al. | |
| D374,469 S | 10/1996 | Barra | |
| 5,613,923 A | 3/1997 | Anliker | |
| 5,820,577 A * | 10/1998 | Taylor | A63B 21/0004 601/40 |
| 5,976,058 A | 11/1999 | Gustafson | |
| 6,361,511 B1 | 3/2002 | Shim | |
| 7,381,156 B2 | 6/2008 | Silagy | |
| 7,731,633 B1 | 6/2010 | Williams | |
| 7,740,561 B2 | 6/2010 | Kupferman | |
| 7,867,145 B2 | 1/2011 | Bearden | |
| 8,601,614 B2 * | 12/2013 | Scaff | A63B 21/4025 2/160 |
| 8,677,514 B1 | 3/2014 | Jones | |
| 8,944,942 B2 | 2/2015 | Oravecz | |
| 9,301,898 B2 | 4/2016 | Cehic | |
| 9,339,690 B1 | 5/2016 | Goldberg | |
| 9,867,473 B1 | 1/2018 | Harrison | |
| D809,614 S | 2/2018 | Chiu | |
| 10,076,143 B2 | 9/2018 | Marriott et al. | |
| 2003/0073939 A1 * | 4/2003 | Taylor | A61H 1/0288 601/40 |
| 2007/0060448 A1 * | 3/2007 | Silagy | A63B 23/16 482/49 |
| 2010/0041521 A1 * | 2/2010 | Ingvast | B25J 9/0006 482/49 |
| 2013/0018289 A1 * | 1/2013 | Nussbaum | A41D 19/0027 601/46 |
| 2013/0219586 A1 * | 8/2013 | Ihrke | B25J 15/08 2/160 |
| 2015/0328492 A1 * | 11/2015 | Marriott | A63B 21/4025 482/124 |

\* cited by examiner

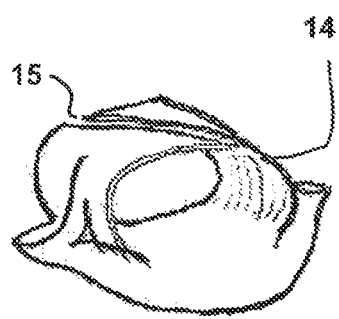
FIG. 2
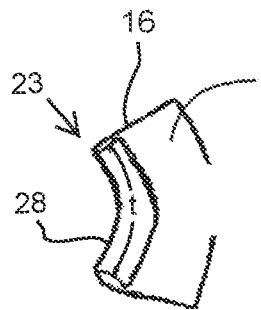
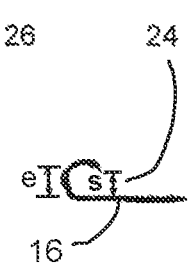
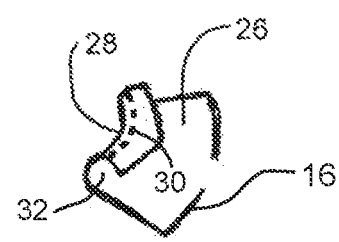
FIG. 3A     FIG. 3B     FIG. 3C

THERAPEUTIC GLOVE FOR SUPPORT AND EXERCISE OF FINGERS AND WRIST

CROSS-REFERENCE TO RELATED APPLICATION(S)

This application is related to U.S. provisional application entitled FLEX GLOVE having Ser. No. 62/707,066, by Felix King III, filed Oct. 20, 2017 and incorporated by reference herein.

BACKGROUND

1. Field

The embodiments discussed herein are directed to a therapeutic glove that provides support and resistance for exercise of hand and forearm muscles and, optionally, massaging pads.

2. Description of the Related Art

There are many kinds of exercise equipment for exercising hand muscles. The best known ones, like stress relief balls and hand grips, increase strength and/or endurance of anterior muscles of the hand used to grip and squeeze. Less common, in part due to the difficulty of providing resistance, is equipment for exercising posterior hand muscles that straighten the fingers and thumbs.

Early examples of equipment for exercising posterior hand muscles are those that attach weights to fingertips, like U.S. Pat. Nos. 623,592 and 2,736,034. Others use miniaturized stretch bands like those used for larger muscles. Rings are slipped over fingers and thumb, like those in U.S. Pat. Nos. 3,612,521 and 5,062,625. Others, like those in U.S. Pat. Nos. 3,347,547; 5,447,490; and 7,740,561, add an attachment to the wrist or palm, so that the thumb is not providing all of the resistance to exercising the fingers.

As known in the field of exercise physiology, varying resistance is essential to develop strength. A variety of techniques are used by devices that exercise posterior hand muscles to provide variation in resistance. Examples include the adjustable elastomeric band in U.S. Pat. No. 4,815,729 and a series of tension-adjusting cleat-lock slots to which elastic members may be detachably connected in U.S. Pat. No. 5,514,052. Other alternatives, such as a dial tensioner, an adjustable knob, and a series of buttons, like those described in U.S. Pat. No. 10,076,143, are similarly complex and expensive to implement.

SUMMARY

An aspect of the therapeutic glove disclosed herein is that ordinary tasks can be performed while the glove provides resistance to posterior hand muscles. This is unlike known devices in which at least a portion of the device, particularly those that provide stretching resistance, extends across the palm of the user.

Another aspect of the therapeutic glove disclosed herein is to provide adjustable resistance by easily changing the number or strength of band(s) that draw fingers and thumb inwards.

In an alternative embodiment, massage pads are included in the glove disclosed herein to relieve soreness of hand and/or wrist muscles.

The above aspects can be attained by an exercise apparatus that includes a glove having a palm, wrist, fingers and a thumb; at least one elastic band; and band guides attached to backs of the fingers of the glove and to the base of the palm of the glove. The at least one elastic band passes through the band guides which allow the at least one elastic band to expand and contract as a wearer of the glove straightens and contracts at least one of fingers and thumb inside the glove.

In an embodiment, the at least one elastic band includes multiple elastic bands and each finger and the thumb of the glove has multiple band guides.

In an embodiment, each of the multiple elastic bands includes at least one continuous elastic band, and each of the band guides on the fingers and the thumb of the glove is a bandlette having a tubular shape with a slit permitting the at least one continuous elastic band to be inserted and removed.

The band guides on the palm of the glove may be palmlettes, each having a hook shape in a cross section perpendicular to a traversal direction of the at least one continuous elastic band guided by the palmlette, the cross section of the palmlette having a width shorter than the palmlette in the traversal direction. A first palmlette is attached to the glove at the base of the thumb and a second palmlette is attached to the palm of the glove adjacent the wrist and below the little finger of the glove.

Each palmlette may be formed as a toroidal section, open along an outer toroidal surface, with a flange extending perpendicular to an inner toroidal surface of the toroidal section.

Inside the glove electric stimulator pads may be mounted, one adjacent to each palmlette, but closer to the center of the palm of the glove.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

In the drawings,

FIG. 2 is a perspective view of an embodiment of a bandlette on the therapeutic glove;

FIGS. 3A-3C are side, end and perspective views of an embodiment of one of the palmlettes on the therapeutic glove;

DETAILED DESCRIPTION OF THE EMBODIMENTS

As illustrated in FIGS. 1A-1D, the therapeutic glove 10 enables a wearer to exercise the posterior (flex) muscles of the hand by attaching elastic bands 12 to the therapeutic glove 10 that cause the fingers to contract toward the palm and provide resistance when the fingers are straightened. The number, placement and strength of the elastic bands 12 may be varied to adjust how the muscles exercised, including the amount of resistance.

Figure 1A:
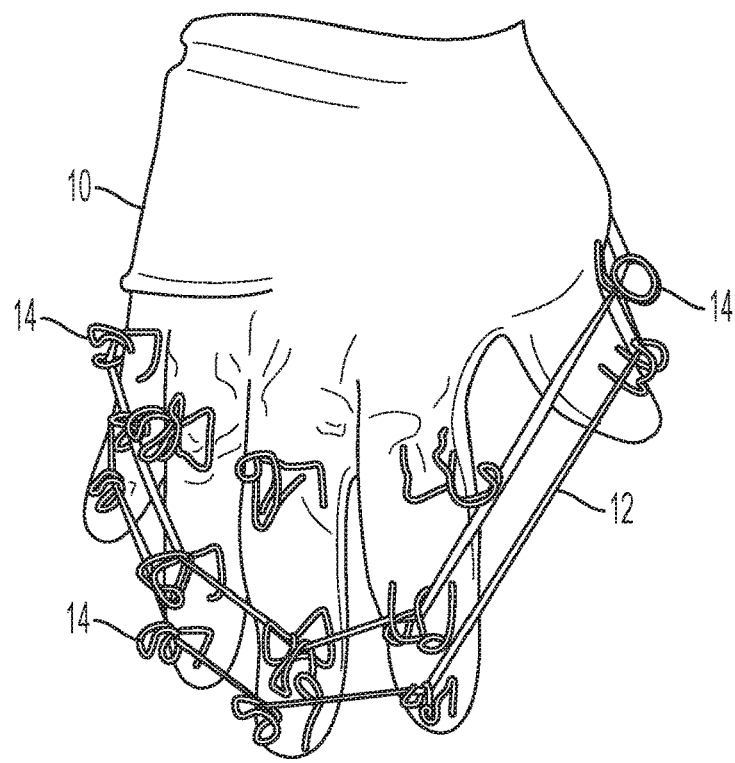
FIGS. 1A-1D are perspective views of an embodiment of the therapeutic glove from back of hand, palm, side and fingers.
Figure 1B:
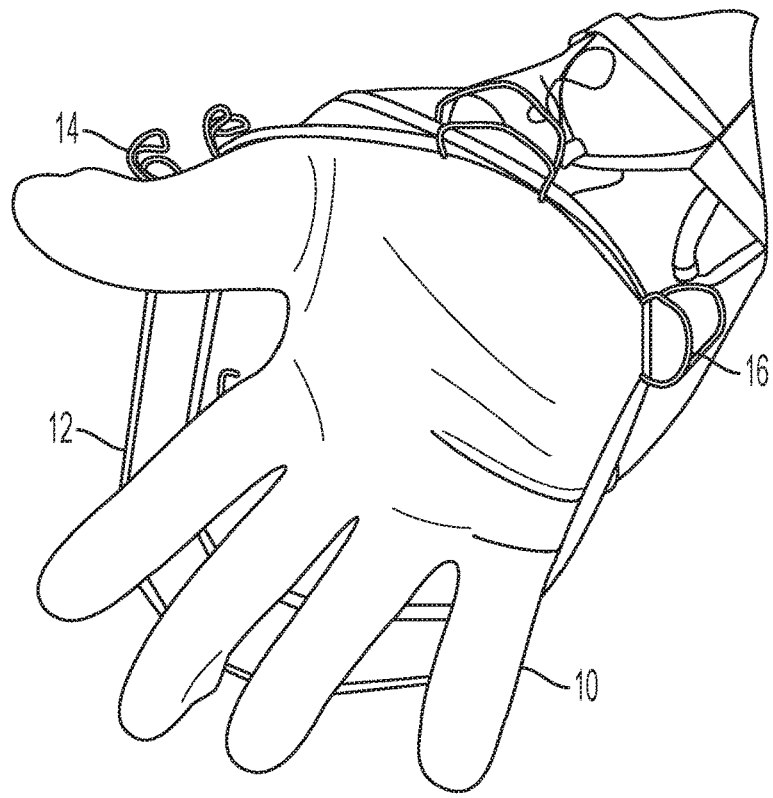
Figure 1C:
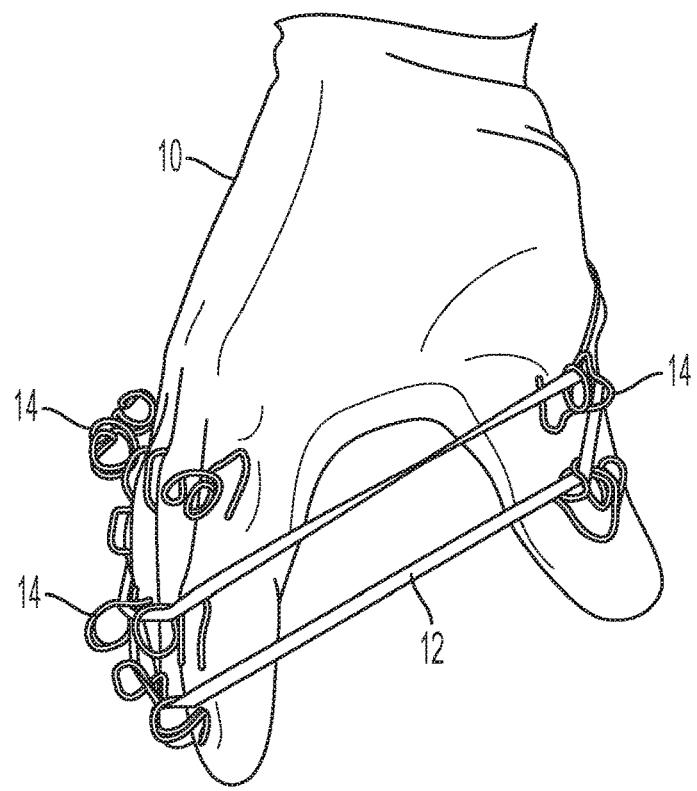
Figure 1D:
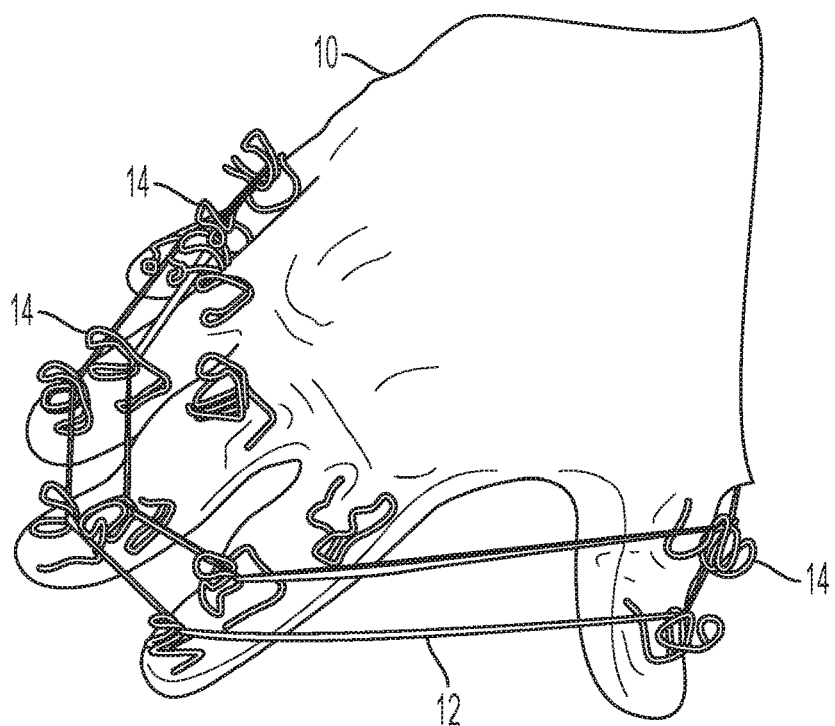

Band guides 14, 16 include bandlettes 14, attached to the fingers and thumb of the therapeutic glove 10 that guide the elastic bands 12 around the outside of the fingers and thumbs. The band guides also include palmlettes 16 attached at the base of the palm, as illustrated in FIG. 1B, to keep the elastic bands 12 clear of the palm while wearing, so that ordinary tasks can be performed while wearing the therapeutic glove 10.

Figure 4A:
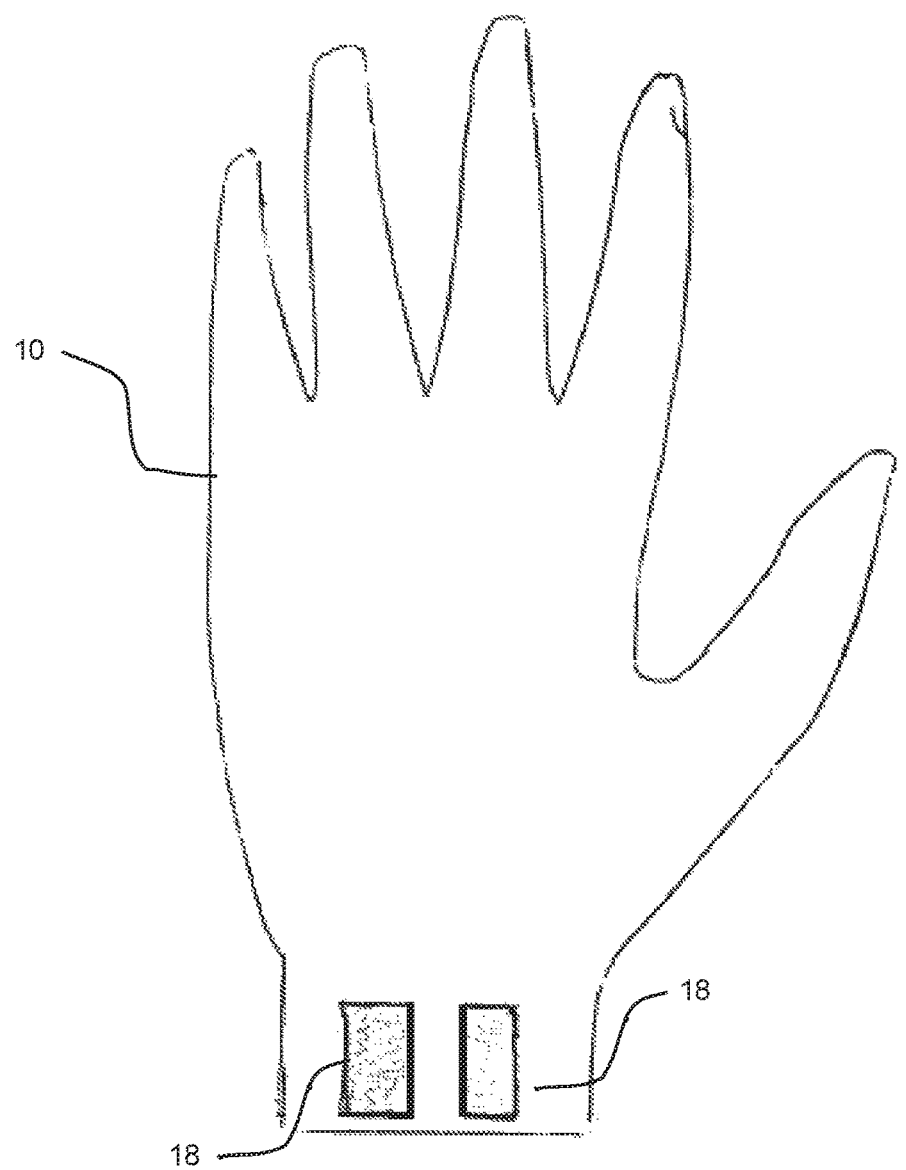
FIGS. 4A and 4C are top views of an embodiment of the therapeutic glove including the wrist strap guides on the inside of the wrist.
Figure 4B:
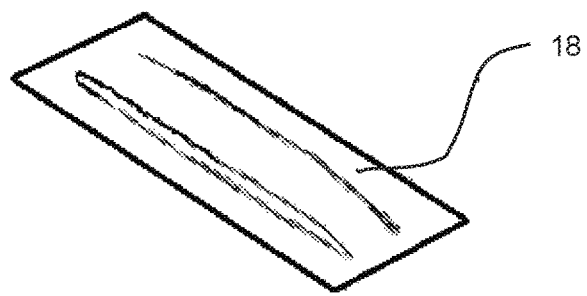
FIG. 4B is a perspective view of an embodiment of one of the wrist strap guides.
Figure 4C:
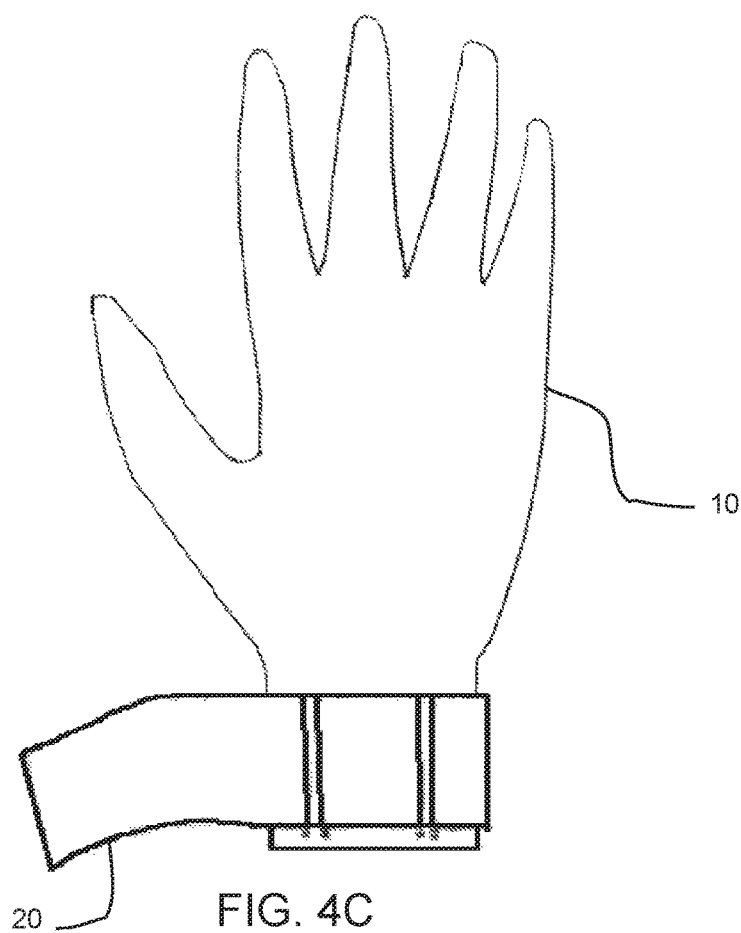
Figure 4D:
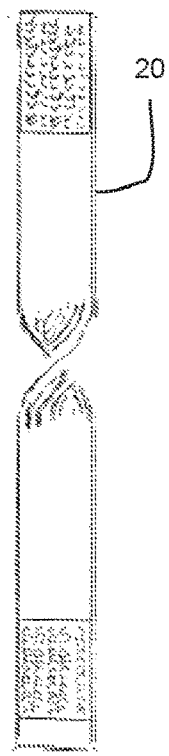
FIG. 4D is a top view of an embodiment of the wrist strap.
Figure 4E:
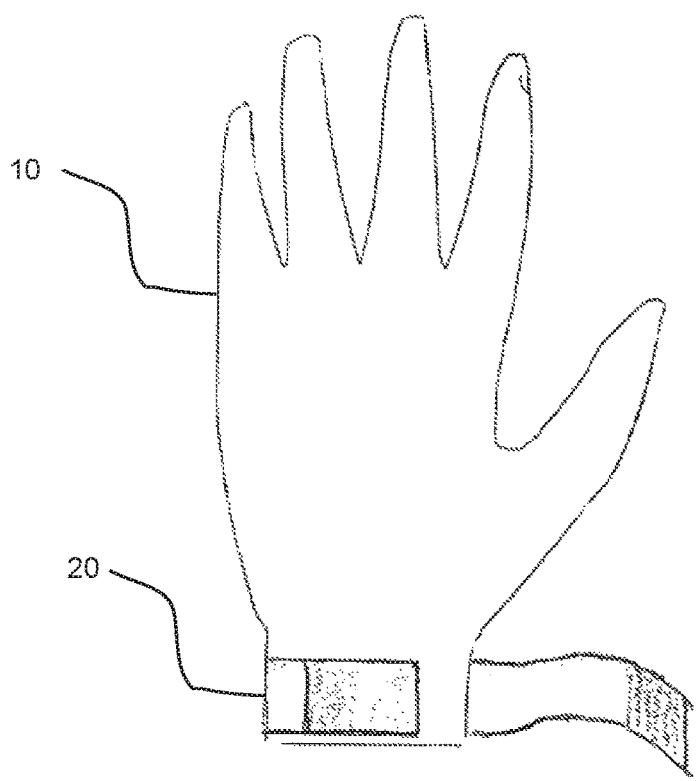
FIG. 4E is a top view of an embodiment of the therapeutic glove including the wrist strap attached to the back of the wrist.

A lightweight glove 10 of any suitable material, such as plastic, nylon, rubber, leather, canvas, etc., may be used. Wrist strap guides 18 (see FIG. 4B) may be aligned with the fingers below the palm of the hand, as illustrated in FIGS. 4A and 4C. Alternatively, the wrist strap guides may be formed in the material of the therapeutic glove 10. The wrist strap 20, illustrated in FIG. 4D may be made of a durable, flexible fabric (canvas or nylon, for example) that is attached to the back of the wrist as illustrated in FIG. 4E and fed through the slits on the front of the therapeutic glove 10 as illustrated in FIG. 4C to provide support for the user.

Figures 5A, 5B:
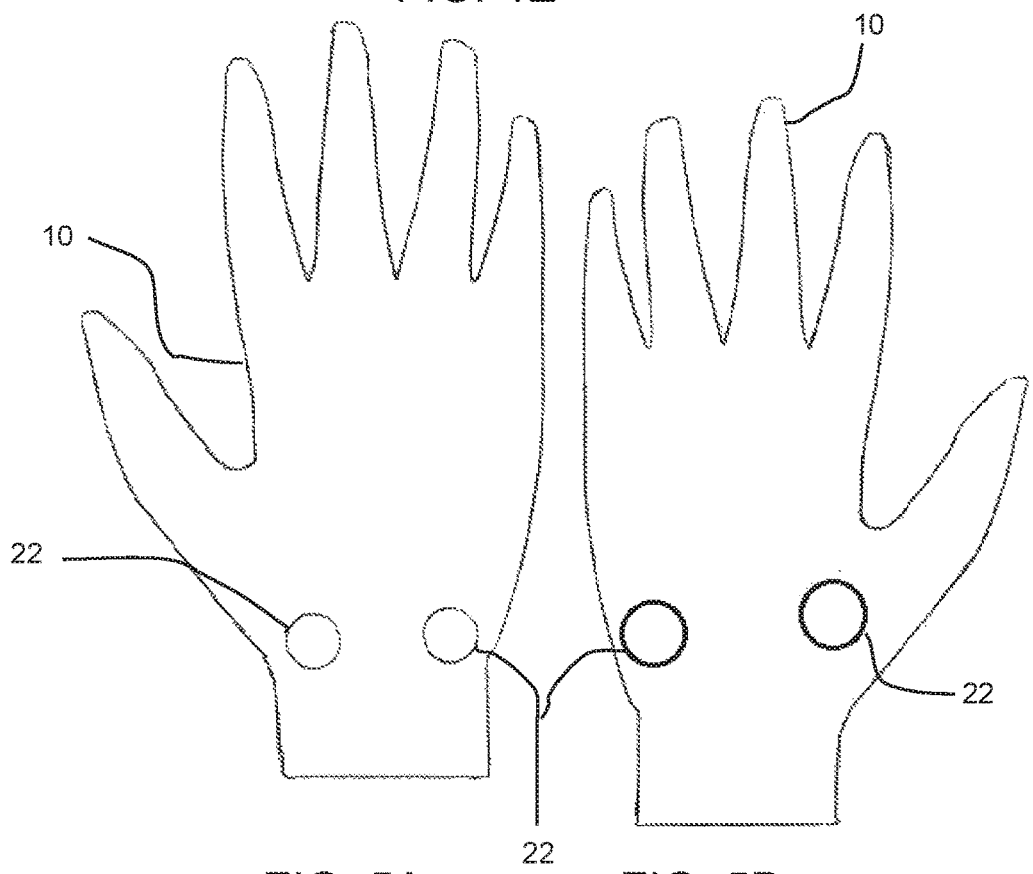
FIGS. 5A and 5B are top views of the palms of right and left therapeutic gloves illustrating placement of electric stimulator massage pads.

In an embodiment, massage pads 22, like those used in an electric stimulator, are attached to the inside of the therapeutic glove 10 at the locations illustrated in FIGS. 5A and 5B. The massage pads 22 may be slightly closer to the palms than the palmlettes 16. These massage pads 22 stimulate muscles to aid in carpal tunnel recovery and prevention.

In an embodiment, the therapeutic glove 10 may be constructed by affixing (e.g., sewing or gluing) reinforcing material inside the therapeutic glove 10 at the location of the wrist strap guides 18 and cutting slits through the glove and reinforcing material to form the wrist strap guides 18. If massage pads 22 are included, they may be attached to the inside of the glove 10 at his time, with the electric pin, jack or wiring towards the glove. After turning all of the exterior of the glove 10 facing outwards, the wrist strap 20 may be attached to the back of the wrist of the glove 10 and fed through the wrist strap guides 18. Hook and loop closures, like those available from Velcro® and/or a buckle of any type may be used to tighten the wrist strap 20.

Next, the bandlettes 14 and palmlettes 16 are attached to the exterior of the glove 10 by sewing or adhesive. As illustrated in FIGS. 1A-3C, the bandlettes 14 and palmlettes 16 may be formed so that continuous elastic bands 12 may be attached, through slits 15 (FIG. 2) in the bandlettes 14 and side openings 24 in the palmlettes 16, in a number and size for desired exercise. Alternatively, the bandlettes 14 and palmlettes 16 may be solid hoops, loops, eyelets or grommets and the elastic bands 12 are fed through the openings therein prior to the ends of the elastic bands being attached in any known way, including tying, adhesive, crimping, etc.

In the embodiment illustrated in FIGS. 3A-3C, each palmlette 16 includes a toroidal section 23 having an inner surface 28 opposite the side opening 24 of size s, and a flange 26 extending perpendicular to the inner surface 28 of the toroidal section. As illustrated in FIG. 3B, this produces a hook shape in a cross section perpendicular to a traversal direction 30 of the elastic band 12 (not shown in FIGS. 3A-3C) guided by the palmlette. As illustrated in FIGS. 3A and 3C, the cross section of the palmlette has an internal width e (i.e., an opening across the hook-shaped cross section), shorter than the length t of the palmlette measured along the traversal direction, resulting in end openings 32 through which the elastic bands pass when in use, as illustrated in FIGS. 1A-1D.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

It will be understood that variations and modifications can be effected within the spirit and scope of the claims which may include the phrase at least one of "A, B and C" as an alternative expression that means one or more of A, B and C may be used, contrary to the holding in Superguide v. DIRECTV, 358 F3d 870, 69 USPQ2d 1865 (Fed. Cir. 2004).

What is claimed is:

1. An exercise apparatus, comprising:
a glove having a palm portion on a first exterior side, a back portion on a second exterior side facing in a direction opposite the palm portion, a wrist portion, a plurality of finger portions, and a thumb portion;
a plurality of continuous elastic bands;
a plurality of first band guides attached to back sides of the plurality of finger portions and to a back side of the thumb portion; and
a plurality of second band guides attached to a base of the palm portion of the glove,
wherein each of the elastic bands pass through a set of the first band guides so as to extend around the back side of each of the finger portions and around the back side of the thumb portion of the glove, thereby allowing the plurality of elastic bands to expand and contract as a wearer of the glove respectively straightens and contracts at least one of a thumb and fingers of the wearer;
wherein each first band guide is formed as a bandlette having a tubular shape with a slit permitting a respective elastic band of the plurality of continuous elastic bands to be inserted into, and removed from, each first band guide.

2. The exercise apparatus according to claim 1, wherein each second band guide is a palmlette such that the plurality of second band guides is a plurality of palmlettes, each palmlette having a hook shape in a cross section perpendicular to a traversal direction of a respective elastic band of the plurality of continuous elastic bands guided by the palmlette, the cross section of the palmlette having an internal width across the hook shape that is shorter than a length of the palmlette in the traversal direction, and
wherein the plurality of palmettes includes a first palmlette attached to the glove at a base of the thumb portion, and a second palmlette attached to the palm portion of the glove adjacent the wrist portion and below a little finger portion of the glove.

3. The exercise apparatus according to claim 2, wherein each palmlette includes a toroidal section with an inner surface, a side opening opposite the inner surface, and a flange extending perpendicular to the inner surface of the toroidal section.

4. The exercise apparatus according to claim 3, further comprising electric stimulator pads mounted inside the glove adjacent to each palmlette, the electric stimulator pads being located closer to a center of the palm portion of the glove than each adjacent palmlette.

\* \* \* \* \*